(12) United States Patent
Egozi

(10) Patent No.: US 8,055,330 B2
(45) Date of Patent: Nov. 8, 2011

(54) SENSING GAS BUBBLES IN A LIVING BODY

(76) Inventor: Noam Egozi, Rehovot (IL)

( * ) Notice: Subject to any disclaimer, the term of this patent is extended or adjusted under 35 U.S.C. 154(b) by 1974 days.

(21) Appl. No.: 10/526,428

(22) PCT Filed: Aug. 28, 2003

(86) PCT No.: PCT/IL03/00707
§ 371 (c)(1),
(2), (4) Date: Feb. 28, 2005

(87) PCT Pub. No.: WO2004/019776
PCT Pub. Date: Mar. 11, 2004

(65) Prior Publication Data
US 2006/0020208 A1 Jan. 26, 2006

Related U.S. Application Data

(60) Provisional application No. 60/406,332, filed on Aug. 28, 2002.

(51) Int. Cl.
*A61B 6/00* (2006.01)

(52) U.S. Cl. ..................................... 600/473; 600/476

(58) Field of Classification Search .......... 600/437–455, 600/473–480
See application file for complete search history.

(56) References Cited

U.S. PATENT DOCUMENTS

| | | | |
|---|---|---|---|
| 3,622,958 A | 11/1971 | Tucker et al. | |
| 3,935,876 A | 2/1976 | Massie et al. | |
| 4,038,976 A | 8/1977 | Hardy et al. | |
| 4,265,251 A * | 5/1981 | Tickner | 600/438 |
| 4,329,054 A * | 5/1982 | Bachalo | 356/336 |
| 4,371,786 A | 2/1983 | Kramer | |
| 4,627,726 A | 12/1986 | Turner | |
| 5,056,357 A | 10/1991 | Dymling et al. | |
| 5,394,732 A * | 3/1995 | Johnson et al. | 73/19.1 |
| 5,862,805 A | 1/1999 | Nitzan | |
| 6,261,233 B1 * | 7/2001 | Kantorovich | 600/454 |
| 6,322,513 B1 * | 11/2001 | Schregel | 600/466 |
| 6,529,751 B1 * | 3/2003 | Van Driel et al. | 600/322 |
| 6,542,761 B1 * | 4/2003 | Jahn et al. | 600/310 |
| 6,699,191 B2 * | 3/2004 | Brock-Fisher | 600/437 |
| 6,875,176 B2 * | 4/2005 | Mourad et al. | 600/442 |
| 6,969,865 B2 * | 11/2005 | Duchon et al. | 250/573 |
| 7,005,107 B2 * | 2/2006 | Breda | 422/73 |
| 7,207,939 B2 * | 4/2007 | Husher | 600/370 |
| 2002/0145122 A1 * | 10/2002 | Duchon et al. | 250/574 |
| 2003/0233044 A1 * | 12/2003 | Brock-Fisher | 600/437 |

OTHER PUBLICATIONS

International Preliminary Examination Report Dated Jun. 3, 2005 From the International Preliminary Examination Authority Re.: Application No. PCT/IL03/00707.
International Search Report Dated Jan. 23, 2004 From the International Searching Authority Re.: Application No. PCT/IL03/00707.
Written Opinion Dated Jan. 21, 2005 From the international Preliminary Examining Authority Re.: Application No. PCT/IL03/00707.

(Continued)

*Primary Examiner* — Sanjay Cattungal

(57) ABSTRACT

A method of detecting gas bubbles in a living body, comprising: transmitting at least one original electromagnetic signal to a body portion; detecting a signal modulated by a flow of blood in said body portion; and analyzing a perturbation in said signal to determine at least one of an existence and a property of a bubble in said blood flow.

70 Claims, 8 Drawing Sheets

OTHER PUBLICATIONS

Office Action Dated Jul. 28, 2008 From the Israeli Patent Office Re.: Application No. 167138.

Response Dated Oct. 21, 2010 to Office Action of Jul. 28, 2008 From the Israeli Patent Office Re.: Application No. 167138.

Communication Pursuant to Article 94(3) EPC Dated Mar. 18, 2011 From the European Patent Office Re. Application No. 03791162.5.

Official Action Dated Oct. 27, 2010 From the US Patent and Trademark Office Re. U.S. Appl. No. 10/526,428.

Office Action Dated Aug. 14, 2011 From the Israeli Patent Office Re.: Application No. 167138 and Its Translation Into English.

Response Dated Sep. 4, 2011 to Communication Pursuant to Article 94(3) EPC of Mar. 18, 2011 From the European Patent Office Re. Application No. 03791162.5.

* cited by examiner

US 8,055,330 B2

SENSING GAS BUBBLES IN A LIVING BODY

RELATED APPLICATIONS

The present application is a US National Phase of PCT Application No. PCT/IL2003/000707, filed on Aug. 28, 2003, published as WO 2004/019776, which is related to and claims the benefit under 35 USC 119(e) of U.S. Ser. No. 60/406,332 filed on Aug. 28, 2002, the disclosure of which is incorporated herein by reference.

FIELD OF THE INVENTION

The present invention relates to sensing gas bubbles in a living body.

BACKGROUND OF THE INVENTION

Various gases are dissolved in the circulatory blood system of living bodies. Changes in ambient pressure can lead to dispersion of gas bubbles from the liquid. At slow pressure changes, the body can expel the bubbles. However at a high rate of change the body cannot expel them fast enough and they can accumulate or grow. Detection of gas bubbles in a living body, at an early stage of accumulating would allow treatment before it is too late.

As an example, people moving quickly from a place of high atmospheric pressure to low atmospheric pressure, would be interested in accurate monitoring of their situation in order to safely control the rate of change. For example, underwater divers use statistical tables to determine the rate at which they can surface from a deep dive instead of measuring their actual physical state. While devices have been described for detection of bubbles in blood, for example in U.S. Pat. No. 6,261,233, the disclosure of which is incorporated herein by reference, which describes an ultrasound system, such devices have apparently not found actual use, especially in underwater situations.

SUMMARY OF THE INVENTION

An aspect of some embodiments of the invention relates to detecting and monitoring gas bubbles within living bodies, based on perturbations in a signal received from a blood flow in the body in which the bubbles are extant and which bubbles cause the perturbations. In an exemplary embodiment of the invention, a living body is radiated, using an electromagnetic wavelength, transparent to the tissue or conduit encasing a fluid (e.g. blood) comprising gas bubbles. The waves are modulated by the flow and are then received and analyzed, for example, to detect perturbations in the expected received signal. Optionally, analysis of the perturbations allows determining the size, rate of growth and/or concentration of the gas bubbles and/or rate of flow of the blood.

In some embodiments of the invention, the measured signal is analyzed based on the amplitudes of the measured signal. Alternatively or additionally, the measured signal is analyzed based on the change in frequency between the transmitted wave and measured wave.

In some embodiments, an optical wave, for example, IR is used, at one or more frequencies. In others, a different wave, for example, visual or RF is used.

It should be noted that electromagnetic wavelengths may be preferred for many uses, for example, underwater, due to the better controllability of the beam, due to the ability to using a coherent signal and/or detection and/or due to the ability of using polarized beams and waves with a controlled bandwidth and/or controlled spatial and temporal profile. Not all of these possibilities are utilized in every embodiment. However, in some cases, the methods described herein may be used for ultrasonic waves. In such waves, frequency processing may be at the level of the pulse rate and/or at the level of actual changes in detected frequencies.

An aspect of some embodiments of the invention relates to real-time provision of monitoring and/or measurement of physiological parameters, in a wide range of situations, for example, underwater, on land and in air or space. Alternatively or additionally to measuring perturbations, other physiological parameters of the body may be detected (and/or changes monitored) from analyzing the waves received from the blood, for example, heart rate, pulse form, respiratory rate, blood pressure, cardiac output, Oxygen saturation (e.g., based on differential absorption at different wavelengths) and blood flow rate and/or volume. In some cases, determining changes in these parameters even for a signal organ provides useful information about the physiological state of the whole body. In an exemplary embodiment of the invention, a gauge for tracking and optionally displaying and or alerting a user is provided. In an exemplary embodiment of the invention, such a gauge is worn by the user on his wrist and tracks bubble information and/or other physiological parameters. Optionally, the gauge can be worn by the person on the wrist, leg, ankle, neck, or chest or on any other part of the body. In some embodiments of the invention the gauge can be used in severe conditions for example, underwater or in outer space.

In an exemplary embodiment of the invention, the gauge is used to provide real-time physiological feedback, for example, underwater so that there is no need to rely on statistical tables to predict the physiological state of a person underwater. Rather, the exact progression for a particular person under particular conditions can be tracked. Possibly, the gauge learns the progression pattern for a person, type of person, starting state and/or planned assignment (e.g., fitness state, starting heart rate and/or other physiological parameters) and uses this pattern to predict problems in a dive. In one embodiment, a statistical progression is calibrated in real-time, for example, times of the progression extended or contracted based on the real-time response of the person doing the activity.

There is thus provided in accordance with an exemplary embodiment of the invention, a method of detecting gas bubbles in a living body, comprising:

transmitting at least one original electromagnetic signal to a body portion;

detecting a signal modulated by a flow of blood in said body portion; and analyzing a perturbation in said signal to determine at least one of an existence and a property of a bubble in said blood flow. Optionally, said original signal comprises a series of pulses. Alternatively or additionally, said detected signal comprises a reflected signal. Alternatively or additionally, said detected signal comprises a signal modulated by transmission through said flow. Alternatively or additionally, said signal comprises a narrow bandwidth signal. Alternatively or additionally, said signal is visible light. Alternatively, said signal is infra-red light.

In an exemplary embodiment of the invention, said signal is at a wavelength which is selectively absorbed by hemoglobin. Alternatively or additionally, said signal is at a wavelength which is selectively reflected by blood vessel walls.

In an exemplary embodiment of the invention, said detected signal is detected using multiple detectors. Alternatively or additionally, said original signal comprises multiple original signals from multiple sources. Optionally, said sources are arranged around a body part in which said bubbles are to be detected. Alternatively or additionally, said sources are arranged to view multiple parts of a body. Alternatively or additionally, said signals are detected in series. Alternatively or additionally, said signals have different wavelengths. Optionally, at least two of said different wavelengths have different absorption properties in blood.

Alternatively or additionally, analyzing comprises combing the effects of said multiple sources.

In an exemplary embodiment of the invention, the method comprises performing AM on said detected signal. Optionally, said AM analysis comprises estimating an unperturbated signal and counting zero crossings relative to said estimation. Optionally, said estimation is selected to preclude the detection of perturbations below a certain threshold. Alternatively or additionally, said estimation comprises an adaptive threshold. Alternatively or additionally, said estimation reduces the effect of systolic-caused changes in said signal.

In an exemplary embodiment of the invention, the method comprises performing FM on said detected signal. Optionally, the method comprises combining said AM analysis and said FM analysis.

In an exemplary embodiment of the invention, the method comprises performing FM on said detected signal. Optionally, said FM analysis comprises applying a frequency transform to said detected signal. Alternatively or additionally, said FM analysis comprises detecting changes in a delay time of a said detected signal relative to said original signal. Alternatively or additionally, said FM analysis comprises detecting a change in amplitude of a frequency component.

In an exemplary embodiment of the invention, the method comprises analyzing said received signal to determine a value or a change in a physiological parameter other than bubbles. Optionally, said physiological parameter comprises a heart rate. Alternatively or additionally, said physiological parameter comprises an oxygen saturation. Alternatively or additionally, said physiological parameter comprises a respiration rate.

In an exemplary embodiment of the invention, said analyzing comprises estimating a number of bubbles. Alternatively or additionally, said analyzing comprises estimating a volume of bubbles. Alternatively or additionally, said analyzing comprises tracking the formation of at least one bubble. Alternatively or additionally, said analyzing estimating a diameter of at least one bubble.

In an exemplary embodiment of the invention, the method comprises estimating a physiological state for diving purposes based on said analysis.

In an exemplary embodiment of the invention, transmitting comprises transmitting when in contact with a skin surface. Alternatively, transmitting comprises transmitting through a layer of water. Optionally, said layer is between 1 and 20 mm thick.

There is also provided in accordance with an exemplary embodiment of the invention, a method of detecting gas bubbles in a living body, comprising:
    transmitting at least one original signal to a body portion;
    detecting a signal modulated by a flow of blood in said body portion; and
    analyzing, using AM analysis, a perturbation in said signal to determine at least one of an existence and a property of a bubble in said blood flow. Optionally, said signal comprises an ultrasonic signal. Optionally, the method comprises applying an FM analysis.

There is also provided in accordance with an exemplary embodiment of the invention, apparatus for bubble detection, comprising:
    at least one electromagnetic signal source adapted to transmit a wave into a body;
    at least one sensor adapted to receive said signal after modulation by a flow in said body; and
    circuitry adapted to analyze said received signal and detect the presence of a bubble in said flow. Optionally, said circuitry is adapted to self-calibrate said apparatus. Alternatively or additionally, said circuitry is adapted to detect if a placement of said device is suitable. Alternatively or additionally, said device is adapted to be worn on a wrist. Alternatively or additionally, said device is adapted for underwater use during diving.

In an exemplary embodiment of the invention, said apparatus comprises a wireless link. Alternatively or additionally, said apparatus comprises a user input for providing task related information.

There is also provided in accordance with an exemplary embodiment of the invention, apparatus for physiological tracking bubble detection, comprising:
    at least one electromagnetic signal source adapted to transmit a wave into a body;
    at least one sensor adapted to receive said signal after modulation by a flow in said body; and
    circuitry adapted to analyze said received signal and detect at least changes in at least two physiological parameters of said body. Optionally, said at least two physiological parameters are selected from a group comprising, existence of bubbles, heart rate, respiration rate, blood pressure, oxygen saturation and vascular response.

There is also provided in accordance with an exemplary embodiment of the invention, a method of bubble tracking in a living body, comprising:
    transmitting at least one original signal to a body portion;
    detecting a signal modulated by a bubble in said body portion; and
    analyzing a perturbation in said signal to determine at least one of an existence and a change in size of a bubble in said body portion.

BRIEF DESCRIPTION OF FIGURES

Particular exemplary embodiments of the invention will be described with reference to the following description of embodiments in conjunction with the figures, wherein identical structures, elements or parts which appear in more than one figure are generally labeled with a same or similar number in all the figures in which they appear, in which.

DETAILED DESCRIPTION OF EMBODIMENTS

General Structure

Figure 1:
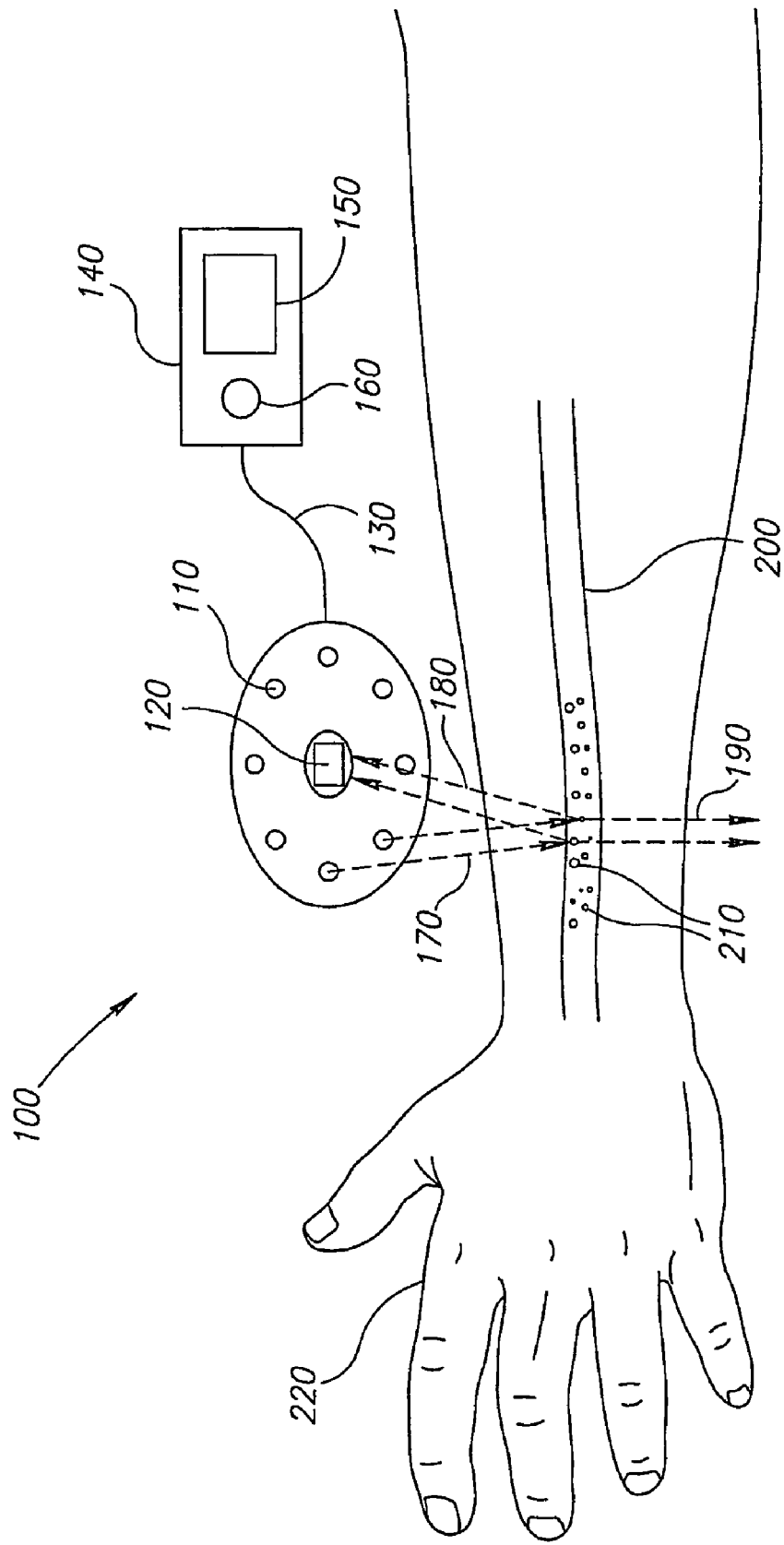
FIG. 1 is a schematic illustrations of a detection device and its use according to an exemplary embodiment of the invention.

FIG. 1 is a schematic illustration of a gas bubble detection device 100, according to an exemplary embodiment of the invention. Detection device 100 transmits an original signal 170, for example a visible light beam toward a living body 220. A sensor 120 in detection device 100 detects and analyses a reflected signal 180. Sensor 120 optionally includes a narrow-bandwidth filter. In some embodiments of the invention, a transmitted signal 190, that passes through body 220 is analyzed instead or in addition. In an exemplary embodiment of the invention, the analyses compares original signal 170 and the received signal. In an exemplary embodiment of the invention, perturbations in sensed signal are analyzed to yield information about gas bubbles 210 found in a flow of blood or other body fluids and/or in non-flowing tissues.

As will be described below various types and wavelengths of waves can be used for signal 170, including, for example, RF, ultrasound and IR. In an exemplary embodiment of the invention, one or more sources 110 are provided for signal 170, for example one or more lasers or LED diodes, which emit signal 170. It should be noted that coherent light is not required in some embodiments and in other embodiments, a relatively wide bandwidth of light, rather than a narrow bandwidth of light, may be used. Also, while a beam is used in some embodiments, in other embodiments, signal 170 may be spread out, patterned and/or focused to a certain area.

In an exemplary embodiment of the invention, signal 170 is radiated toward a conduit 200, for example a blood vessel (e.g. vein or artery). In an exemplary embodiment of the invention, signal 170 is of a type and/or wavelength which passes substantially unattenuated (or only partially attenuated to a fixed degree) through tissue of the living body. Optionally, signal 170 wave is reflected from blood and also reflected by gas bubbles. Alternatively or additionally, signal 170 penetrates blood but is absorbed or scattered by gas bubbles. Alternatively, signal 170 penetrates gas bubbles but is absorbed or scattered by blood. Differential effects of the blood and bubbles on signal 170 are optionally used as described below. Also, differential effects for different wavelengths may be used, for example as described below. In some embodiments of the invention, the effect on the signal by movement of the blood and/or gas bubbles is used.

In some embodiments of the invention one or both of the following effects are used: differences in amplitude caused by existence of gas bubbles and differences in frequency shifts or profiles caused by existence of gas bubbles. It is noted that in some embodiments the growth of gas bubbles can be detected, possibly even in stationary tissue.

In an exemplary embodiment of the invention, the sensed signal exhibits a generally sinusoidal shaped graph, representing the systolic wave of the living body. However, as noted below, this general shape may be analyzed to determine additional information. Further, for perturbation analysis, a moving threshold or frequency filter may be used which effectively hides the generally sinusoid shape.

In some embodiments of the invention, signal sensor 120 comprises an electromagnetic sensor such as a photodiode, PIN diode or a CCD. Optionally, sensor 120 is connected to an electronic circuit 140, which analyzes the sensed signal. The results are then optionally displayed to a user on a display 150 or as an audio signal on a speaker 160, for example by a series of beeps or a voice speaking out values.

Figure 2:
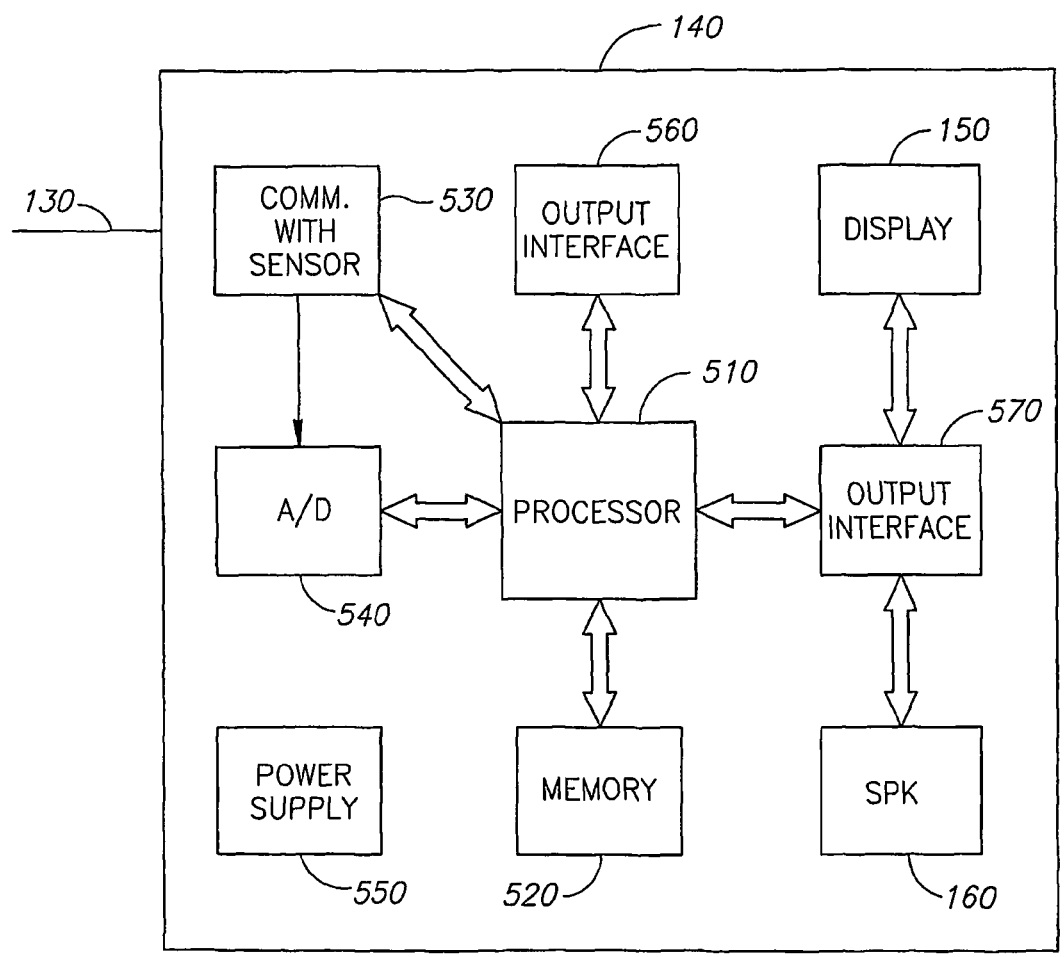
FIG. 2 is schematic block diagram of a circuit for the detection device of FIG. 1, in accordance with an exemplary embodiment of the invention.

FIG. 2 is schematic block diagram of a circuit 140 according to an exemplary embodiment of the invention. In an exemplary embodiment of the invention, circuit 140 comprises a processor 510 which controls the device and analyzes the sensed signals. Separate processor or other circuit types may be used instead. Circuit 140 receives measurements on a communication interface 530 from sensor 120, for example using an external cable 130, an internal bus and/or using a wireless connection. While interface 530 is optional, it may be used to reject some signals or for communicating with sensor 120. An analog to digital converter 540 converts the received signal, optionally only if the signal is within a given range.

In an exemplary embodiment of the invention, circuit 140 comprises a power source 550 (e.g. a battery) to supply power for detector 100. Optionally, the device has a user input 560 (e.g. a switch) to turn detection device 100 on and off, and optionally, select modes of operation, for example display modes for display 150 or for selecting sensed physiological parameters.

In an exemplary embodiment of the invention, device 100 comprises an output interface 570, which controls output to display 150, speaker 160 and other outputs, such as an interface to an external computer using a USB connection, wireless connection (e.g., BlueTooth), serial connection or parallel connection. In some embodiments of the invention, device 100 is used for remote monitoring of the physiological state of a person (e.g. in a dangerous environment).

In some embodiments of the invention, circuit 140 comprises a direct body interface, for example an electric shock device or pricking device to arouse a person's attention in case of deterioration of their physical state.

Amplitude Analysis

In an exemplary embodiment of the invention, detection device 100 applies amplitude analysis on the reflected signal 180 and/or transmitted signal 190 (i.e., sensed signals) to determine the existence of gas bubbles and provide other physiological parameters as described below.

FIGS. 3A, 3B, 3C and 3D are schematic graphs, illustrating the amplitude of the original signal and the sensed signal, in accordance with an exemplary embodiment of the invention.

Figure 3A:
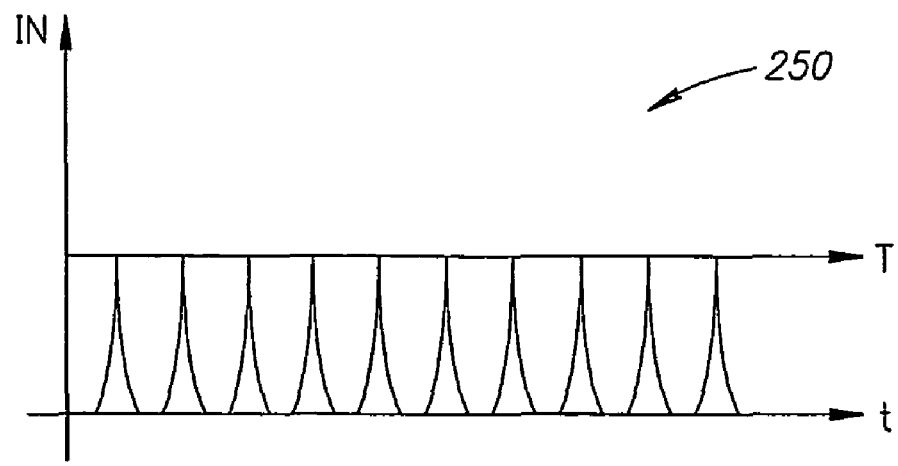
FIGS. 3A, 3B, 3C and 3D are schematic graphs, illustrating the amplitude of transmitted waves and detected wave, in accordance with an exemplary embodiment of the invention.

In an exemplary embodiment of the invention, original signal 170 is transmitted as a series of short pulses of a fixed amplitude, at a selected rate (for example, 1 Mz) from one or more sources into the living body. Graph 250 of FIG. 3A shows the amplitude of the original signal 170 as a function of time. Other pulse frequencies may be used as well, for example in the range of 100 kHz to 6 GHz. As noted below, the amplitude may be non-constant.

Figure 3B:
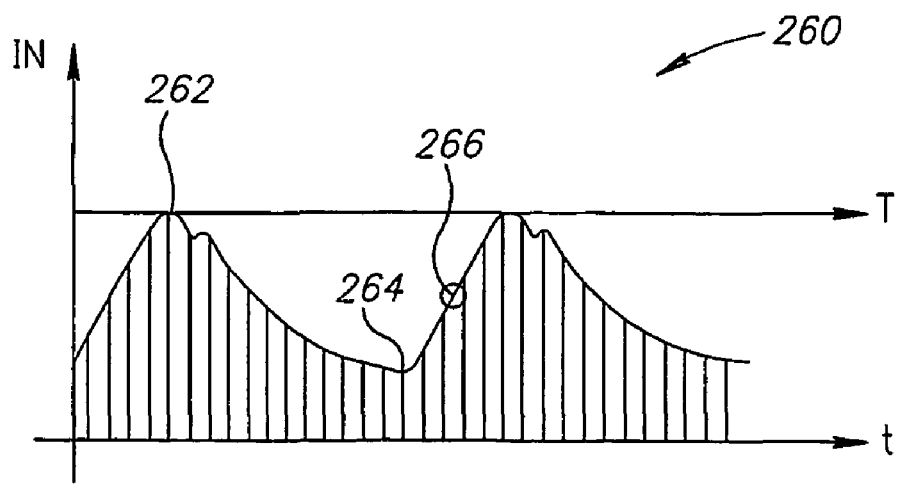

Graph 260 of FIG. 3B shows a sensed signal (e.g., 180 in FIG. 1) as a function of time. In an exemplary embodiment of the invention, as explained above the resulting measured amplitudes render a generally sinusoidal shaped graph. It is expected that the generally sinusoidal shaped graph comprises small perturbations from a smooth systolic wave due to the effect of gas bubbles 210. Other possible sources of such perturbations include noise and movement artifacts.

Graph 270 is a magnified view of a short segment 266 of graph 260. The magnified view reveals the perturbations to the amplitude of the systolic wave some of which are caused by the existence of gas bubbles.

Figure 3C:
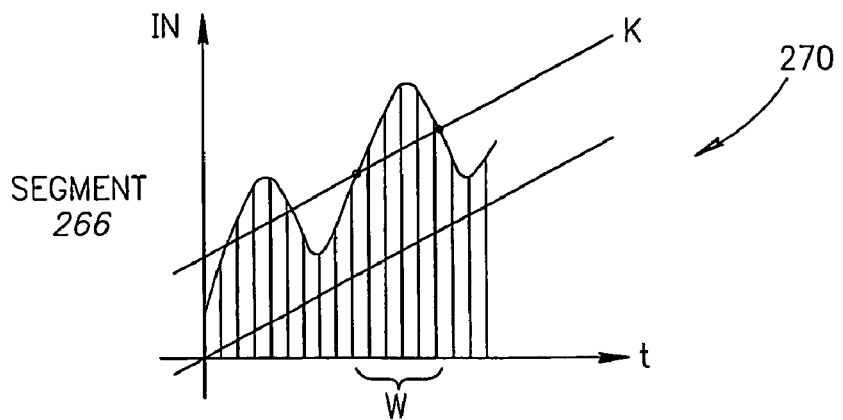

Graph 280 shows the perturbations in graph 270 of FIG. 3C normalized relative to the systolic wave in order to simplify the explanation and generally in accordance to the effect of using a moving threshold as described below.

What is described now is for the case where reflection (typically scattering) from a gas bubble is greater than that for blood. A similar but modified analysis may be used for opposite cases or for transmitted signals.

The amplitude at a specific time in graph 280 is affected by the existence of one or more bubbles and may be proportional to the size of the bubbles at the measured point. Alternatively, the total area between two zero crossings may be related to the bubble size. The change in time of the amplitude illustrates the gas bubble flow at the point being measured. In some embodiments of the invention, a bubble increases the measured amplitude, for example the amplitude measured from a reflected wave 180. In some embodiments of the invention, a bubble reduces the measured amplitude, for example in measuring a transmitted wave, which is weakened by passing through the bubble in passing through body 220.

It should be noted that the effect of bubble size and/or number may be non-linear with regard to number and/or volume. It should also be noted that in case the bubbles are uniform and dense in the blood flow, it is possible that the perturbations may be smaller than if there are fewer bubbles or the bubbles be undetected. However, for physiological reasons, once the bubbles are substantially uniform in the blood, the patient is in grave danger, if not already dead. It should also be noted that the formation of a new bubble in a clear blood flow will also generally cause a perturbation. It is expected that the perturbations detected grow (even if not linearly) from the point where there is no danger at least until a danger point beyond which an exact measurement is not really useful. In any case, the detection device can be calibrated for different conditions and even be calibrated to differentially detect a small number of perturbations when the total reflectance is large (signifying many bubbles) than when the total reflection is lower (signifying fewer bubbles). Additionally, other processing methods as described below may be used.

Figure 3D:
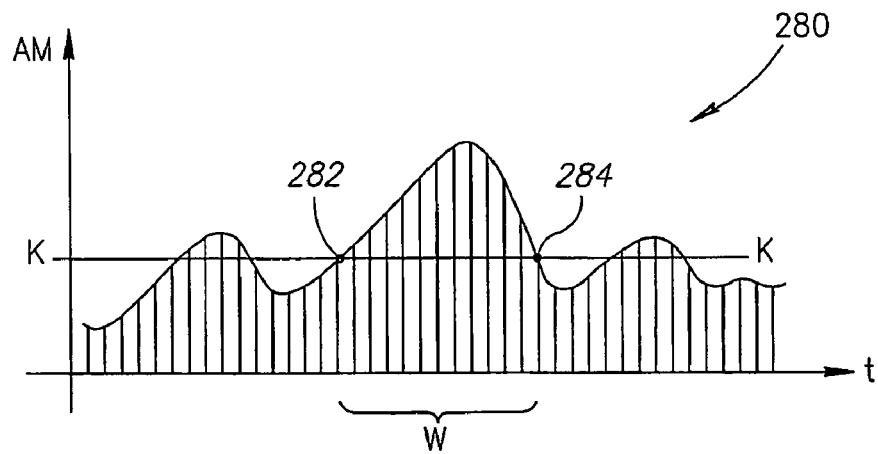
Figure 3E:
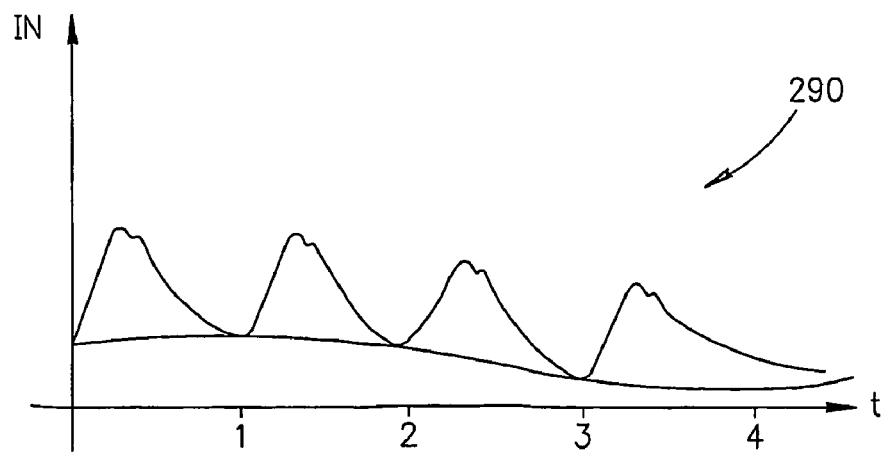
FIG. 3E shows the effect of a breathing cycle on the measured signal.

In an exemplary embodiment of the invention, a measured amplitude may be incorrect due to noise in the system. A low amplitude value may be a result of noise and not related to gas bubbles, whereas a high amplitude value would probably be at least in part related to gas bubbles. Optionally, a threshold value is selected in order to limit the analysis to larger amplitude values which are clearly related to bubbles. In FIG. 3C and FIG. 3D a threshold line K is passed through graphs 270 and 280 respectively.

Typically the threshold value is selected to leave 80% of the measured amplitudes above line K. Optionally, this value is continuously updated by taking into account the average deviation of the amplitudes in the graph from this value, resulting in the majority of points being above the threshold. Points on the graph that cross line K are referred to as crossing points, for example points 282 and 284 in graph 280 of FIG. 3D. The crossing points mark the beginning and end of a gas bubble (or group of bubbles) of sufficient size to be taken into account. The number of bubbles over a specific time is equal to half of the number of crossing points over that time. In some embodiments of the invention, two or more smaller bubbles may be referred to as one larger bubble, if the resulting amplitudes are not accurate enough to differentiate. In some cases, as described below, viewing form multiple angles, for example, 90, 280, 270 or more, such as 350 or 360 may be used. The number of transmitted pulses between two crossing points result in a value proportional to the volume of the bubble (W). In an exemplary embodiment of the invention, the use of an adaptive threshold causes the threshold line to follow the systolic wave, thereby eliminating its effect. Alternatively or additionally, frequency filtering techniques may be used.

In some case, what is determined is the diameter of the bubble, which may be dependent on the amplitude of the perturbation. Changes in this diameter, for example at several points along the flow, or as a function of time, may be an indication of bubble growth. Total bubble volume may be provided in some cases by integrating the positive portion of the perturbations over a item period.

In some embodiments the minimum size of a bubble which can be detected is dictated by the wavelength used, for example, to be more than 0.5*0.3 microns, for an 0.3 micron wavelength.

It should be noted that depending on the signals used and area being sensed what may be measured is actually groups of bubbles rather than single bubbles. However, if only simple assumptions are made about the bubble distribution, for example that the bubbles act in a statistically regular manner (e.g., even random distribution), the number of groups of bubbles and their sizes are expected to correlate with the physiological state. It should also be noted that statistical analysis of the "volume" of the bubbles may also be used to help count bubbles, by assuming (e.g., based on calibration tests) a certain distribution and correcting for it.

It should be noted that the area being viewed by sensor 120 and illuminated by signal 170 may encompass more than one blood vessel. furthermore, as described below, signals may be purposely detected from different sized blood vessels and/or static tissue. In each such detected signal, the above described processing may be applied albeit, optionally with different calibration.

This analysis allows detecting bubbles. Additionally, this analysis gives an approximation to the number and/or volume of bubbles in a time period and/or flow volume (if blood flow volume is also estimated).

Frequency Analysis

Figure 4:
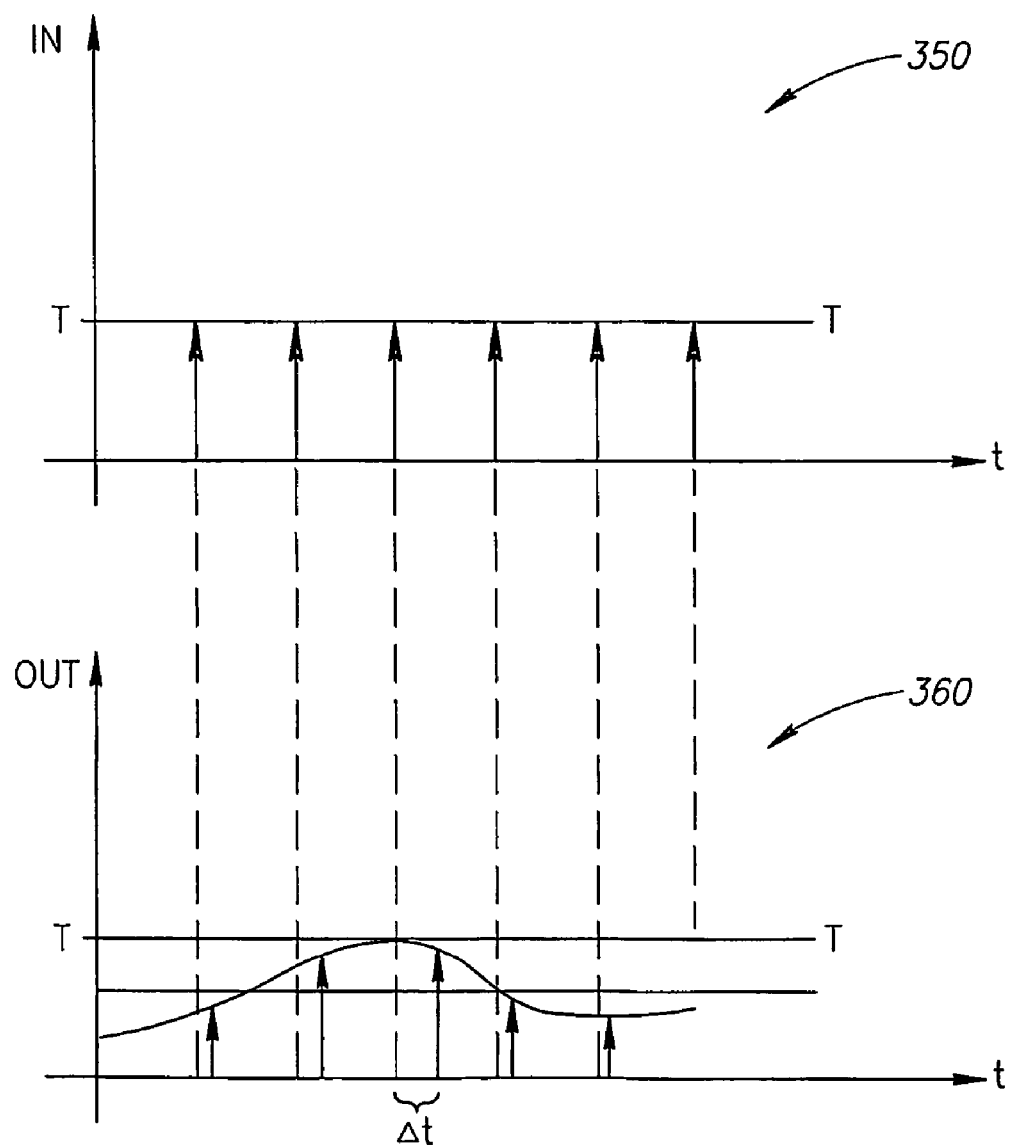
FIG. 4 is an illustration of two schematic graphs, illustrating the time domain of transmitted waves and detected waves, in accordance with an exemplary embodiment of the invention.

FIG. 4 shows two schematic graphs 350 and 360, illustrating the time domain of transmitted waves and detected waves, in accordance with an exemplary embodiment of the invention.

Graph 350 of FIG. 4 shows the amplitude versus time of the pulses of transmitted electromagnetic wave 170. Graph 360 of FIG. 4 shows the amplitude of the pulses of the measured electromagnetic wave (180, 190) as a function of time, for one exemplary embodiment of the invention. The comparison of graph 360 with graph 350 shows a shift in the reception time of the received pulses relative to their expected reception time. This shift depends on the speed of the reflecting object, in that different speeds generate different time shifts. It should be appreciated that blood flows at a range of distances and at a range of speeds, thus providing a certain profile of time shifts. However, a bubble, reflects a significantly greater amount of energy (in some embodiments) and/or may move at a different speed than the rest of the flow, thereby changing the frequency profile of the reflection.

The frequency shift is a result of the Doppler effect caused by sampling the moving blood flow and gas bubbles. In addition, newly formed bubbles are also visible. A gas bubble may precipitate from the blood flow as a result of changes in the ambient pressure on the blood vessel, tissue and/or for other reasons. The gas bubble initially clings to the walls of the blood vessel and then accelerates with the blood flow until it reaches the speed of the blood flow. In an exemplary embodiment of the invention, analysis of the frequency shift reveals a sinusoidal pattern of growing and diminishing shift size. Optionally, the accelerating gas bubbles 210 cause perturbations to this simple pattern. Alternatively or additionally, existing bubbles can cause turbulence and/or change their speed, such as when they bounce into wall, cling momentarily and/or otherwise move erratically. Alternatively or additionally, it is noted that blood flow in arteries is pulsate in general and the blood may accelerate with each pulse at a different speed form the bubbles.

In an exemplary embodiment of the invention, time shift analysis comprises noting changes in the reflection time for one or more pulses and/or performing statistical analyses on them. Alternatively or additionally, a frequency transform, such as Fast Fourier Transform (FFT) or a Wavelet Transform are performed on the signal. The result is a frequency profile which, as noted above, can be expected to change as a function of the bubbles. In some embodiments, what is analyzed is not changes in the frequency profile but rather the amplitude of the different frequencies, for example a spike in a certain frequency can indicate a sudden large reflection of an object (e.g., a bubble) at a certain speed. Counting such spikes can give an indication of a number of bubbles and/or be used to correct the amplitude analysis for the effects of noise.

It should be noted that the results from different analysis types may be combined, for example, using AM analysis to detect when a bubble exists and FM analysis to determine its size and/or abnormal propagation.

Determining Other Information from the Measured Signals

Alternatively or additionally, other physiological parameters and/or changes therein of living body 220, may be determined from the sensed signal, for example systolic wave, blood pressure, heart rate, cardiac output, respiratory rate, possibly an indication of respiratory capacity or changes therein and vascular resistance. Following are details explaining how these physiological parameters can be determined from the measurements of device 100.

Graph 260 of FIG. 3 optionally, shows the systolic wave. The extreme points (e.g. 262 and 264) of the systolic wave (in graph 260) optionally, show the change in blood pressure, for example passing from high to low between point 262 to 264. The number of maximum points (e.g. point 262) over a period of time optionally, give the heart rate. Integration between two points on graph 260 optionally, gives the cardiac output of the measured point over the selected time. While a complete cardiac output requires monitoring all the blood flow, for example at the aorta, changes in the flow to an organ, such as the hand, may correlate with various physiological conditions, such as reduced cardiac output, shock, or extreme exercise.

In an exemplary embodiment of the invention, the respiratory rate is also available from the measured wave shown in graph 260. As described above, the systolic wave is the carrier for the gas bubble perturbations (graph 270). Likewise the systolic wave is a modulation of a respiratory wave which forms a somewhat sinusoidal base for the systolic wave, as shown in a graph 290 of FIG. 3E. Suitable spatial filtering of the sensed signal will provide the respiratory rate. For example, the systolic rate is between 5 and 300 pulses per minute and the respiratory rate is between 2 and 0.1 pulses per second An estimate that is somewhat correlated with the respiratory capacity is determined by integrating over the respiratory wave.

The systemic vascular resistance (SVR), which is the resistance to the blood flow is optionally determined by rate of change of the slope of the systolic wave (dP/dt for a point P'). With:

$$SVR = E*P'/(dp/dt), E=(dp/dt)dt \text{ for a point } p'$$

$$SVR = \text{rate of change*pressure at point/slope}$$

A blood pressure may be measured using an oscillometric method. Alternatively or additionally, changes in blood pressure are monitored. Alternatively or additionally, a calibration value may be measured prior to use, for example using a standard blood pressure measurement device.

In some embodiments of the invention, detection device 100 allows a user to select the physiological parameters that will be analyzed, for example using user input 560. In some embodiment of the invention, detection device 100 can analyze interrelated parameters to determine a users condition and/or verify integrity of the measurements. In an exemplary embodiment of the invention, one or more rules or formula are programmed into device 100 to describe the relationship between physiological parameters. Alternatively or additionally, a user may be required to enter one or more values, for example, physical fitness or degree of prior exercise. In an exemplary embodiment of the invention, device 100 may be used to monitor physiological parameters of the body and indicate where certain action, such as pausing assent in diving, should be taken or is imminent. While device 100 may utilize standard time based table, in an exemplary embodiment of the invention, device 100 relays at least in part on actual physiological measurements, such as detection of bubbles or reduction in cardiac output instead of or in addition to such standard tables.

Optionally, the user can select, which parameter or parameters will be displayed and/or the method of display, for example a graph, a single changing value, an audio message or sound and/or direct stimulation, for example electrical or tactile stimulation.

In some embodiments of the invention, specific parameters can be selected to give an alert to the user (or to a remote user, for example, via an umbilical cable) on specific "higher level" states, for example, stress which can be identified by high pulse rate, high respiratory rate, and change in systolic rate or cardiac output. Stress is just one example of states that can be defined based on the interaction of multiple parameters and/or integration of multiple parameters. In particular, it is noted that changes in one parameter may modify the meaning of other parameters, for example, a reduction in respiratory rate may reduce oxygen saturation on its own even without additional factors and thus, is optionally used to correct the interpretation of the oxygen saturation parameter.

Exemplary Method of Utilization

Figure 5:
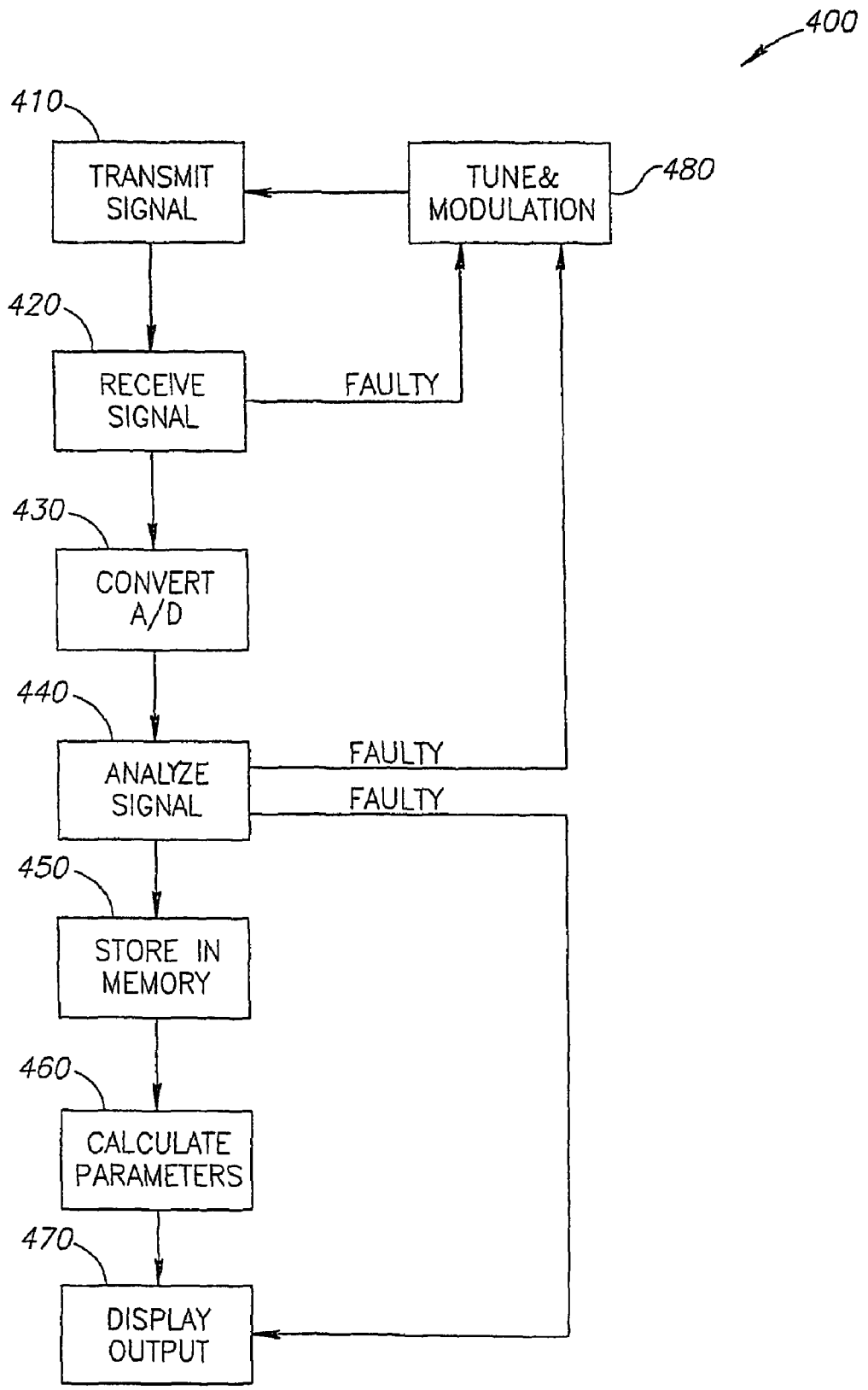
FIG. 5 is a flow diagram of the process of detecting gas bubbles according to an exemplary embodiment of the invention.

FIG. 5 is a flow diagram 400 of the process of detecting gas bubbles according to an exemplary embodiment of the invention. Detection device 100 transmits (410) a signal (170, FIG. 1) to measure a flow of gas bubbles 210 in living body 220. Detection device 100 receives (420) a signal (180, FIG. 1) reflected from the blood flow in body 220. In some embodiments of the invention, the received signal is used to initially (and/or later and/or periodically) adjust the transmitted signal. In some embodiments of the invention, the measured signal is analyzed to determine if it conforms to a basic form. If the signal does not conform to the basic form, this may indicate in correct placement of the device and/or incorrect signal parameters. Optionally (480) calibration information is sent to transmitter 110 and/or sensor 120.

The calibration information can adjust parameters such as one or more of:

a. The frequency of the transmitting pulses, by raising or lowering the pulse rate, variable rate may be used.
b. The amplitude of the transmitted pulses, by raising or lowering the power supplied to the signal sources 110, variable amplitude may be used.
c. The noise threshold, by raising the selected threshold value as described above.
d. The type of modulation, for example pulse CW, chirp, monopulse, AM and/or FM, which may instead be fixed.
e. Selecting different sensors for sampling the signal, in an embodiment using multiple sensors as described below.

In some embodiments of the invention, detection device 100 signals the user to adjust the physical position of the sensor, for example after failing to receive an acceptable signal despite changing controllable parameters.

Optionally, if an analog signal is used it is converted 430 to a digital signal for processing. Alternatively, the receiver samples the received signal directly as a digital signal using a digital sensor. Alternatively, analog processing may be provided.

In some embodiments of the invention, the digital information is analyzed (440), for example to check that the information is a logical measurement comprising meaningful information. Optionally, (440) prevents accepting illogical information, which can be caused for example by detection device 100 being knocked out of position or an external flash of light.

In some embodiments of the invention, received measurements (and/or determined physiological data) that are not found to be faulty are stored (450) in memory 520. Optionally, the analysis in (440) is performed on the current information and also takes into account information stored in memory 520 (FIG. 2), for example to check that the current measurements are logical in view of the previous measurements.

The information stored in memory is optionally used to calculate (460) physiological parameters, for example, the number of gas bubbles, the size of the gas bubbles, the rate of flow of the gas bubbles, the growth in the rate of flow of bubbles and growth in the number of bubbles as a function of time as described above. Calculated parameters are then output (470) for the user to view, for example by showing the values on display 150, or reading out the values on speaker 160, or flashing light or beeping at a selected pace in order to pass on the information to the user of the system. In some embodiments of the invention, a graph is shown on display 150 to illustrate the status of a selected parameter. Optionally, a user can select the parameter to be displayed, for example using a selection button as described above.

If however the information during the analysis (440) is found to be faulty then the information is optionally analyzed by processor 510 to determine if adjustments need to be made as described above. Alternatively or additionally, processor 510 will notify the user to check device 100 and fix the problem, for example by displaying a message (460) on display 150 and/or speaker 160.

Other Embodiments

Optionally, the wavelength of the light is selected from wavelengths, which are not hazardous to the body, for example the LED diodes may transmit light of wavelengths of 400-1500 nanometers, emitting light that is visible to the human eye or light that is non visible to the eye. Alternatively or additionally, a hazardous wavelength can be radiated at a very short pulse length with a momentary high energy, giving an average energy value close to zero so that there is minimal interaction with body 220.

In some embodiments of the invention the wavelength is selected according to the part of the body being analyzed, or the element that is of interest, for example a wavelength of 540 nanometers is specifically affected by Hemoglobin causing a sharper measured signal. Other wavelengths, for example between 300 and 1500 nm, may be used. In another example, a wavelength of 810 nm shows the effect of the systolic wave by reflection from the body of the blood vessel and may be used, for example, to provide information about vascular compliance or about the actual systolic wave form. A wavelength of 950 nm may be sensitive to movement of the sensor, thus allowing movement artifacts to be recognized and ignored, in other wavelengths. A wavelength of 1100 nm may show movement artifacts like the 950 nm wavelength, without a contribution of the outside of the movement of the blood vessel. Higher wavelengths may be useful for viewing into and through fat tissue. Oxygen saturation may be detected and/or monitored if several wavelengths are used, for example as well known in the art. Such saturation monitoring may be especially useful for diving with abnormal partial oxygen pressure and/or in general for detecting changes in Oxygen saturation as a function of partial Oxygen pressure. Multiple wavelengths maybe also be used to determine the effect of intervening tissue, possibly transmitted in parallel or in series to each other. Alternatively or additionally, different wavelengths may have opposite interactions with blood and bubbles, for example one wavelength being reflected by bubbles and another absorbed. Further, different wavelengths may be used for transmission and for reflection. Multiple wavelengths may also be used for viewing different tissue depths, with different wavelengths being capable of penetrating different amounts. The angles between the transmitter and receiver for such wavelengths may take this distance into account. Also different wavelengths may be used for different body structures, for example larger blood vessels, arteries, veins and capillary tissue may use different wavelengths to assist differentiation. Multiple detectors may be used, or a single detector may be shared. In one embodiment of the invention, a wavelength which is not differentially affected by blood and tissue is used to calibrate the signal levels.

In FIG. 1 sensor 120 is shown in the center of the light sources to sense reflected light 180, however sensor 120 may be positioned elsewhere such as opposite the light sources, on the other side of living body 220 in order to sense transmitted signals 190.

Figure 6A:
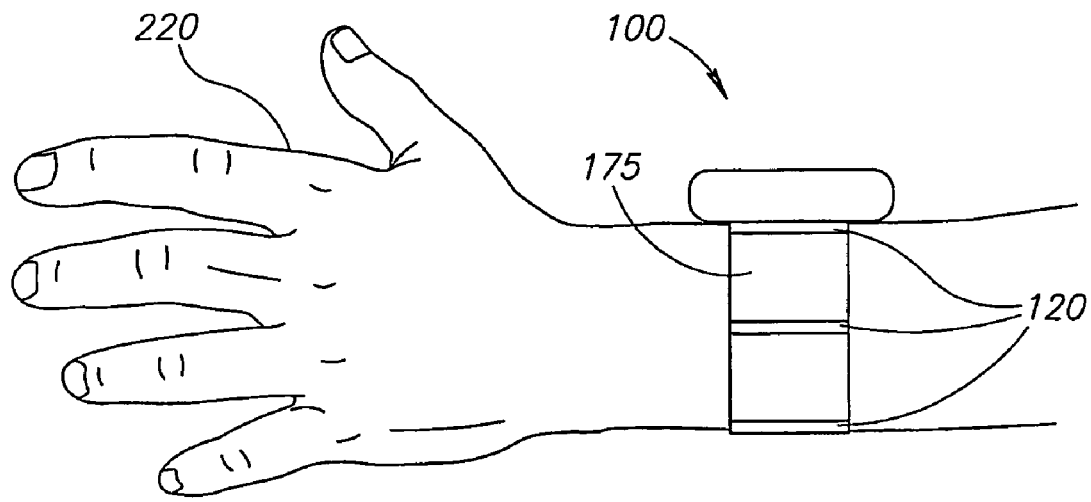
FIGS. 6A and 6B are schematic illustrations of a detection device and its deployment according to an exemplary embodiment of the invention.
Figure 6B:
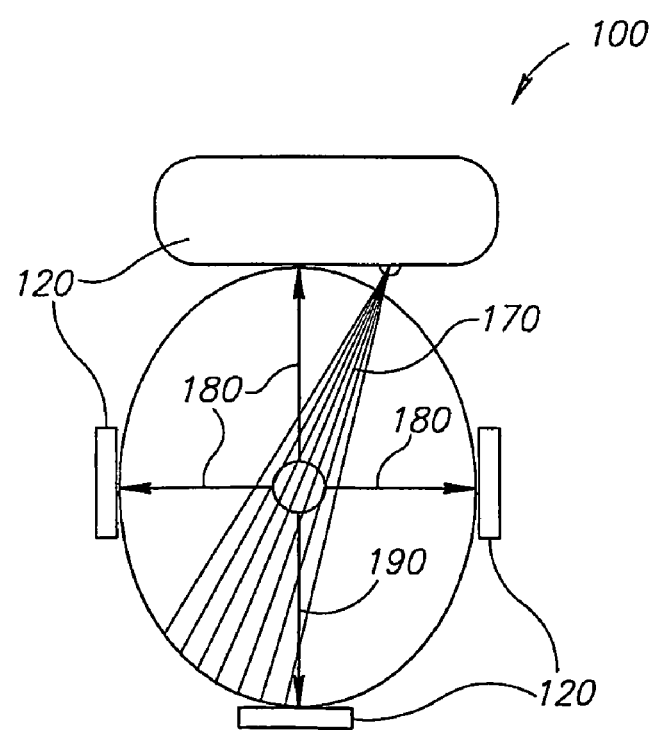

FIGS. 6A and 6B are schematic illustrations of a detection device and its deployment according to an exemplary embodiment of the invention. In some embodiments of the invention, as shown in FIGS. 6A and 6B, multiple sensors (and/or multiple sources) are used, to allow device 100 to select the sampling point, for example if a specific sensor does not give acceptable results. Alternatively or additionally, device 100 can sense signals using multiple sensors 120 and optionally, average over the results of several sensors or compare the results of different sensors used on the same body. For example, 2, 3, 4 or more sensors may be used. Alternatively or additionally, for example, 2, 3, 4 or more sources may be used.

Alternatively or additionally, the use of multiple sensors allows some shadowing artifacts to be overcome. Alternatively or additionally, a relatively large sensor is used which can detect light reflected from multiple locations, possibly overcoming some shadowing effects as well.

While not shown, in some embodiments of the invention, the sources 110 and/or sensor 120 may be physically aimed, for example manually using a small screw and/or electrically using a motor. Scanning at different angles may be used to establish a viewing area with sufficient blood flow and/or blood flow of a desired type, such as veins, arteries and/or small vessels. Such scanning may be manual or automatic, depending on the embodiment.

In an exemplary embodiment of the invention, as shown in FIG. 6B multiple sensors 120 are provided, which may sense reflected waves 180 and transmitted waves 190 and/or sense waves scattered at various scattering angles.

In some embodiments of the invention, source 110 and/or sensor 120 are positioned so that the signal travels in a direction having a component parallel to the direction of motion of gas bubbles 210, to better provide a Doppler effect. Alternatively or additionally, any Doppler shift in the perpendicular direction is from turbulence and/or an erratically moving bubble.

In some embodiments of the invention, the device is shaped as a wristwatch (as shown in FIG. 6A) or a necklace (not shown), wherein all parts of the device are worn close to the body. Optionally, the light source and sensor are adhesively attached to body 220, for example using tape. Alternatively, detection device 100 can be kept in place by a strap or band 175. A coupling gel is optionally provided to ensure good optical contact between device 100 and the skin. Alternatively, for example underwater, measurement through the water, for example between 0.1 and 10 cm, for example 2 cm, is provided. In some embodiments, the water itself serves as a coupling layer and no separate gel layer is required. Alternatively, a layer of transparent silicone or other gel-like material is provided on the outside of device 100, to contact the skin. Alternatively, tight attachment of device 100 to the body substantially precludes the existence of a water layer between device 100 and the body. Measurement through the air is also possible for some wavelengths, optionally using a coherent light source. for some types of materials and/or wavelengths, measurement through clothes is also possible.

In some embodiments of the invention, electronic circuit 140 is attached on the same band as sensor 120 or even in the same encasement as the light sources 110 and sensor 120. Alternatively or additionally, electronic circuit 140 may be placed in a position with easy access for the user, while the measuring part is placed where it can conveniently measure, for example electronic circuit 140 may be worn on a user's wrist and the light sources 110 and sensor 120 may be worn on a user's stomach or ankle. Optionally, when initially, placing device 100, the user is required to adjust its position until receiving a satisfactory signal on the display. Alternatively or additionally, when using multiple sensors, a sensor with a good signal can be selected from among the sensors without needing to adjust the sensors. Alternatively, the signals from multiple sensors and/or sources can be combined and/or averaged. Optionally, sensor 120 is provided as a linear or 2D array of sensors, rather than as a scalar sensor as in some embodiments. Different elements of the array may be adapted for different wavelengths.

When contributions from multiple signals are combined, the combination may be, for example at the signal level, after sensing, after A/D conversion and/or after processing. in some cases, the combination takes the form of using one result to check the reliability of other results. It should be noted transmitted and reflected effects can be combined, for example, by averaging the bubble count of each.

Figure 6C:
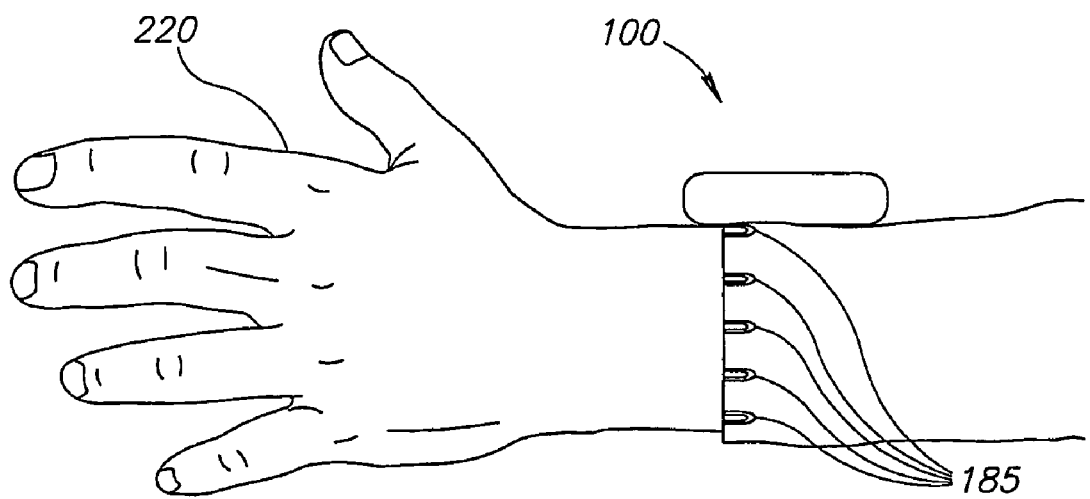
FIG. 6C is a schematic illustration of a detection device deployed in accordance with an alternative embodiment of the invention.

FIG. 6C shows an embodiment where the circuitry of device 100 fits over clothes, while one or more sensors and/or light sources fit under the cloths, for example, as one or more clips 185. This embodiment may be used for a diving suit. Optionally, a small hole in the suit is provided for a wire or the wire passes through a zipper area (not shown).

In some embodiments of the invention, detection device 100 is sealed in a protective encasement or prepared from parts that are water resistant and/or durable under high pressure, so that detection device 100 can be used under severe conditions, such as during diving underwater. In an exemplary embodiment of the invention, the protective construction of detection device 100, allows use of the device to measure physiological signs and gas bubbles under water and/or in outer space. In an alternative embodiment of the invention, device 100 is provided as a component of a dive computer to assist with the calculations indicated by statistical tables.

In an exemplary embodiment of the invention, the device can be coupled to an external computer using output interface 570, for example using a wired or wireless link.

In an exemplary embodiment of the invention, sensor 120 samples more than one point and/or samples an area, this allows further confirmation of the accuracy of the measurements and/or allows to provide an average. Optionally, the relative measurement of flow between multiple sensed points along the path of conduit 200 allow calculation of the rate of flow of the bubbles and their density in the blood stream using AM modulation and comparing between the points.

It should be noted that although in the above description reference is made primarily to electromagnetic waves, other types of waves of various wave-forms can be used, for example audio waves of various wavelengths (e.g. ultrasonic).

As noted above, calibration may be performed, for example, by taking a measurement prior to diving or by comparing to the results of a calibrated device (e.g., using a computer link between the two devices). Alternatively or additionally, calibration is carried out after measurement, for example in the middle or after a dive, and used to analyze previously stored data. Alternatively or additionally, a lower quality calibration is done in the field and a higher quality calibration is done in a laboratory. It is noted that for some uses all that is required is monitoring of changes relative to the starting state.

It will be appreciated that the above described methods may be varied in many ways, including, changing the order of steps, and the exact implementation used. It should also be appreciated that the above described description of methods and apparatus are to be interpreted as including apparatus for carrying out the methods and methods of using the apparatus.

The present invention has been described using non-limiting detailed descriptions of embodiments thereof that are provided by way of example and are not intended to limit the scope of the invention. It should be understood that features and/or steps described with respect to one embodiment may be used with other embodiments and that not all embodiments of the invention have all of the features and/or steps shown in a particular figure or described with respect to one of the embodiments. Variations of embodiments described will occur to persons of the art. Section titles are provided for clarity and do not necessarily limit the contents of the section to the use of the title.

It is noted that some of the above described embodiments may describe the best mode contemplated by the inventors and therefore may include structure, acts or details of structures and acts that may not be essential to the invention and which are described as examples. Structure and acts described herein are replaceable by equivalents which per-form the same function, even if the structure or acts are different, as known in the art. Therefore, the scope of the invention is limited only by the elements and limitations as used in the claims. When used in the following claims, the terms "comprise", "include", "have" and their conjugates mean "including but not limited to".

The invention claimed is:

1. A method of detecting gas bubbles in a living body, comprising:
   transmitting at least one original electromagnetic signal to a body portion;
   detecting said signal modulated by a flow of blood in said body portion; and
   analyzing a perturbation in said detected signal to determine at least one of an existence and a property of a bubble in said blood flow,
   wherein said transmitting, said detecting and said analyzing are carried out by a device worn on said body.

2. A method according to claim 1, wherein said original signal comprises a series of pulses.

3. A method according to claim 1, wherein said detected signal comprises a reflected signal.

4. A method according to claim 1, wherein said detected signal comprises a signal modulated by transmission through said flow.

5. A method according to claim 1, wherein said signal comprises a narrow bandwidth signal.

6. A method according to claim 1, wherein said signal is infra-red light.

7. A method according to claim 1, wherein said signal is at a wavelength which is selectively absorbed by hemoglobin.

8. A method according to claim 1, wherein said signal is at a wavelength which is selectively reflected by blood vessel walls.

9. A method according to claim 1, wherein said detected signal is detected using multiple detectors.

10. A method according to claim 1, wherein analyzing comprises combing the effects of said multiple sources.

11. A method according to claim 1, wherein said signal is at a wavelength suitable for viewing through fat tissue.

12. A method according to claim 1, done under water, in the air or in outer space.

13. A method according to claim 1, wherein transmitting comprises transmitting through air.

14. A method according to claim 1, wherein transmitting comprises transmitting through clothing.

15. A method according to claim 1, wherein transmitting comprises transmitting through an intermediate layer.

16. A method according to claim 1, wherein said signal is at a wavelength which is sensitive to motion of the sensor.

17. A method according to claim 16, wherein the wavelength is not selectively reflected by blood vessel walls.

18. A method according to claim 1, wherein transmitting comprises transmitting through a layer of water.

19. A method according to claim 18, wherein said layer is between 1 and 20 mm thick.

20. A method according to claim 1, wherein said original signal comprises multiple original signals from multiple sources.

21. A method according to claim 20, wherein said sources are arranged around a body part in which said bubbles are to be detected.

22. A method according to claim 20, wherein said sources are arranged to view multiple parts of a body.

23. A method according to claim 20, wherein said signals are detected in series.

24. A method according to claim 20, wherein said signals have different wavelengths.

25. A method according to claim 24, wherein at least two of said different wavelengths have different absorption properties in blood.

26. A method according to claim 25, wherein the different wavelengths respond differently to bubbles.

27. A method according to claim 25, also comprising using the signals of different wavelengths for one or more of estimating an effect of intervening tissue, looking at different depths in tissue, and looking at the flow of blood in different sized blood vessels.

28. A method according to claim 1, wherein said signal is visible light.

29. A method according to claim 28, wherein said analyzing comprises estimating a number of bubbles.

30. A method according to claim 28, wherein said analyzing comprises estimating a volume of bubbles.

31. A method according to claim 28, wherein said analyzing comprises tracking the formation of at least one bubble.

32. A method according to claim 28, wherein said analyzing estimating a diameter of at least one bubble.

33. A method according to claim 28, wherein transmitting comprises transmitting when in contact with a skin surface.

34. A method according to claim 28, wherein analyzing comprises estimating a growth rate of bubbles.

35. A method according to claim 28, comprising estimating a physiological state based on said analysis, in air or in outer space.

36. A method according to claim 28, comprising estimating a physiological state using multiple measured parameters, taking into account the interaction of the parameters.

37. A method according to claim 28, comprising estimating a physiological state for diving purposes based on said analysis.

38. A method according to claim 37, comprising using a change in the physiological state to predict problems during a dive, and to indicate where certain action should be taken or is imminent.

39. A method according to claim 38, wherein the change in the physiological state comprises one or more of appearance of bubbles, reduction in cardiac output, and increase in stress.

40. A method according to claim 38, wherein using the change in the physiological state to predict problems comprises adapting the prediction to a person doing the diving based on a real-time response of the person.

41. A method according to claim 28, comprising performing AM on said detected signal.

42. A method according to claim 41, wherein said AM analysis comprises estimating an unperturbated signal and counting zero crossings relative to said estimation.

43. A method according to claim 42, wherein said estimation is selected to preclude the detection of perturbations below a certain threshold.

44. A method according to claim 42, wherein said estimation comprises an adaptive threshold.

45. A method according to claim 42, wherein said estimation reduces the effect of systolic-caused changes in said signal.

46. A method according to claim 41, comprising performing FM on said detected signal.

47. A method according to claim 46, comprising combining said AM analysis and said FM analysis.

48. A method according to claim 28, comprising performing FM on said detected signal.

49. A method according to claim 48, wherein said FM analysis comprises applying a frequency transform to said detected signal.

50. A method according to claim 48, wherein said FM analysis comprises detecting changes in a delay time of a said detected signal relative to said original signal.

51. A method according to claim 48, wherein said FM analysis comprises detecting a change in amplitude of a frequency component.

52. A method according to claim 28, comprising analyzing said received signal to determine a value or a change in a physiological parameter other than bubbles.

53. A method according to claim 52, wherein said physiological parameter comprises a heart rate.

54. A method according to claim 52, wherein said physiological parameter comprises an oxygen saturation.

55. A method according to claim 52, wherein said physiological parameter comprises one or both of a respiration rate and a respiratory capacity.

56. A method according to claim 55, wherein the physiological parameter comprises a respiration rate, and determining the value or change in the physiological parameter comprises determining the respiration rate from a measured systolic wave.

57. A method according to claim 52, wherein said physiological parameter comprises one or more of a pulse form, a cardiac output, a blood flow rate, a blood volume, a blood pressure, and a systemic vascular resistance.

58. A method according to claim 57, wherein the physiological parameter comprises a local blood flow rate to an organ, and the method also comprises using a change in the local blood flow rate to estimate a change in a physiological condition of the body as a whole.

59. A method according to claim 52, wherein a user selects one or more such physiological parameters.

60. A method according to claim 59, also comprising displaying one or more such physiological parameters selected by the user.

61. A method of detecting gas bubbles in a living body, comprising:
    transmitting at least one original optical signal to a body portion;
    detecting a signal modulated by a flow of blood in said body portion; and
    analyzing, using AM analysis, a perturbation in said signal to determine at least one of an existence and a property of a bubble in said blood flow,
    wherein said transmitting and analyzing are by a wearable device.

62. A method according to claim 61, comprising applying an FM analysis.

63. Wearable apparatus for bubble detection, comprising:
    at least one electromagnetic signal source adapted to transmit a wave into a body;
    at least one sensor adapted to receive said signal after modulation by a flow in said body; and
    circuitry adapted to analyze said received signal and detect the presence of a bubble in said flow.

64. Apparatus according to claim 63, wherein said circuitry is adapted to self-calibrate said apparatus.

65. Apparatus according to claim 63, wherein said circuitry is adapted to detect if a placement of said device is suitable.

66. Apparatus according to claim 63, wherein said wave is optical and wherein said device is adapted to be worn on a wrist.

67. Apparatus according to claim 63, wherein said wave is optical and wherein said device is adapted for underwater use during diving.

68. Apparatus according to claim 63, comprising a wireless link.

69. Apparatus according to claim 63, comprising a user input for providing task related information.

70. A method of bubble tracking in a living body, comprising:
    transmitting at least one original electromagnetic signal to a body portion;
    detecting said signal modulated by a bubble in said body portion; and
    analyzing a perturbation in said detected signal to determine at least one of an existence and a change in size of a bubble in said body portion,
    wherein said transmitting, detecting and analyzing are performed by a wearable device.

* * * * *